United States Patent [19]

Mito

[11] Patent Number: 6,001,774
[45] Date of Patent: Dec. 14, 1999

[54] HERBICIDAL COMPOSITION

[75] Inventor: Nobuaki Mito, Kobe, Japan

[73] Assignee: Sumitomo Chemical Company, Limited, Osaka, Japan

[21] Appl. No.: 09/071,540

[22] Filed: May 4, 1998

[30] Foreign Application Priority Data

May 6, 1997 [JP] Japan ................................. 09-115699
May 6, 1997 [JP] Japan ................................. 09-115701

[51] Int. Cl.$^6$ .......................... A01N 43/84; A01N 43/824
[52] U.S. Cl. ............................................................ 504/130
[58] Field of Search ............................................. 504/130

[56] References Cited

U.S. PATENT DOCUMENTS

| | | | |
|---|---|---|---|
| 4,640,707 | 2/1987 | Nagano et al. | 71/96 |
| 5,047,080 | 9/1991 | Yoshida et al. | 71/96 |
| 5,858,920 | 1/1999 | Dahmen et al. | 504/103 |

OTHER PUBLICATIONS

*The Pesticide Manual*, 10$^{th}$Edition, pp. 489–490, 1994.
*Brighton Crop Protection*, Crop Protection Conference, Weeds — 1995 Proceedings, vol. 1, pp. 43–48.

*Primary Examiner*—S. Mark Clardy
*Attorney, Agent, or Firm*—Birch, Stewart, Kolasch & Birch, LLP

[57] ABSTRACT

A herbicidal composition is described, which contains as active ingredients, (a) N-(7-fluoro-3,4-dihydro-3-oxo-4-prop-2-ynyl-2H-1,4-benzoxazin-6-yl)cyclohex-1-ene-1,2-dicarboxamide (i.e, flumioxazin) and (b) 4'-fluoro-N-isopropyl-2-(5-trifluoromethyl-1,3,4-thiadiazol-2-yloxy) acetanilide (i.e, fluthiamide). The herbicidal composition is useful for effective control of a wide variety of weeds in upland fields, particularly in corn fields and in soybean fields. Also described are a weeding method with the above herbicidal composition; and use as a herbicide, of a mixture of the above active ingredients.

11 Claims, No Drawings

HERBICIDAL COMPOSITION

TECHNICAL FIELD

The present invention relates to a herbicidal composition.

BACKGROUND ART

At the present time, numerous herbicides are commercially available and they are widely used. There are, however, many species of weeds to be controlled and their growth extends over a long time. For this reason, requested are herbicides with higher herbicidal activity, wide herbicidal spectrum, and safety to crops.

DISCLOSURE OF INVENTION

The present inventor has intensively studied to find out excellent herbicides. As a result, he has found that various weeds which grow or will grow in crop lands or non-crop lands can be effectively controlled by soil or foliar treatment of these weeds with a herbicidal composition containing as active ingredients, N-(7-fluoro-3,4-dihydro-3-oxo-4-prop-2-ynyl-2H-1,4-benzoxazin-6-yl)cyclohex-1-ene-1,2-dicarboxamide (common name flumioxazin; hereinafter referred to as flumioxazin) and 4'-fluoro-N-isopropyl-2-(5-trifluoromethyl-1,3,4-thiadiazol-2-yloxy)acetanilide (hereinafter referred to as fluthiamide).

He has further found that the herbicidal activity is synergistically increased as compared with the cases where the active ingredients are independently used, and that the herbicidal spectrum is expanded and a wide variety of weeds can be selectively controlled, particularly in corn fields or soybean fields, thereby completing the present invention.

Thus, the present invention provides a herbicidal composition comprising as active ingredients, flumioxazin and fluthiamide (hereinafter referred to as the present composition); and a weeding method therewith.

MODE FOR CARRYING OUT THE INVENTION

Flumioxazin which is one active ingredient of the present composition is a compound as described in The Pesticide Manual 10th edition (published by British Crop Protection Council, 1994), at page 489.

Fluthiamide which is another active ingredient of the present composition is a compound as described in Brighton Crop Protection Conference Weeds-1995 Proceedings Volume 1 (published by The British Crop Protection Council, 1995), at page 44.

The present composition has a herbicial activity against a wide variety of weeds and a selectivity between crop and weeds, therefore, is excellent as a herbicide. In particular, the herbicidal composition of the present invention effectively controls the main weeds in corn fields and in soybean fields, e.g., dicotyledonous plants such as wild buckwheat (*Polygonum convolvulus*), pale smartweed (*Polygonum lapathifolium*), pennsylvania smartweed (*Polygonum pensylvanicum*), common purslane (*Portulaca oleracea*), common lambsquarters (*Chenopodium album*), redroot pigweed (*Amaranthus retroflexus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), ivyleaf morningglory (*Ipomoea hederacea*), tall morningglory (*Ipomoea purpurea*), entireleaf morningglory (*Ipomoea hederacea* var. *integriuscula*), jimsonweed (*Datura stramonium*), black nightshade (*Solanum nigrum*), common cocklebur (*Xanthium strumarium*), common sunflower (*Helianthus annuus*), field bindweed (*Convolvulus arvensis*), sun spurge (*Euphorbia helioscopia*), devils beggarticks (*Bidens frondosa*), and common ragweed (*Ambrosia artemisiifolia*); and monocotyledonous plants such as barnyardgrass (*Echinochloa crusgalli*), green foxtail (*Setaria viridis*), giant foxtail (*Setaria faberi*), yellow foxtail (*Setaria glauca*), southern crabgrass (*Digitaria ciliaris*), goosegrass (*Eleusine indica*), johnsongrass (*Sorghum halepense*), quackgrass (*Agropyron repens*), and shattercane (*Sorghum bicolor*), while it exhibits no significant phytotoxicity on crops such as corn and soybean. The present composition exhibits an excellent herbicidal activity in non-tillage cutivation as well as in usual tillage cultivation.

In the present composition, the mixing ratio of flumioxazin to fluthiamide, although it may vary with the species of weeds to be controlled, situation and conditions of application, and other factors, is usually in the range of 1:0.1 to 1000 by weight, preferably in the range of 1:0.1 to 50 by weight.

The present composition may be usually used in the form of formulations such as emulsifiable concentrates, wettable powders, flowables and granules which can be prepared by mixing the composition with solid carriers, liquid carriers, or other bulking agents, and if necessary, adding surfactants or other adjuvants to this mixture. In such a formulation, flumioxazin and fluthiamide are usually contained at the total amount of 0.5 to 90 wt %, preferably 1 to 80 wt %.

The solid carrier to be used in the formulation may include, for example, the following materials in fine powder or granule form: clays (e.g., kaolinite, diatomaceous earth, synthetic hydrated silicon oxide, Fubasami clay, bentonite, acid clay); talc and other inorganic minerals (e.g., sericite, powdered quartz, powdered sulfur, activated carbon, calcium carbonate); and chemical fertilizers (e.g., ammonium sulfate, ammonium phosphate, ammonium nitrate, ammonium chloride, urea). The liquid carrier may include, for example, water; alcohols (e.g., methanol, ethanol); ketones (e.g., acetone, methyl ethyl ketone, cyclohexanone); aromatic hydrocarbons (e.g., toluene, xylene, ethylbenzene, methylnaphthalene); non-aromatic hydrocarbons (e.g., hexane, cyclohexane, kerosine); esters (e.g., ethyl acetate, butyl acetate); nitrites (e.g., acetonitrile, isobutyronitrile); ethers (e.g., dioxane, diisopropyl ether); acid amides (e.g., dimethylformamide, dimethylacetamide); and halogenated hydrocarbons (e.g., dichloroethane, trichloroethylene).

The surfactant may include, for example, alkylsulfate esters; alkylsulfonate salts; alkylarylsulfonate salts; alkyl aryl ethers and their polyoxyethylene derivatives; polyethylene glycol ethers; polyhydric alcohol esters; and sugar alcohol derivatives.

The other adjuvants may include, for example, adhesive agents and dispersing agents, such as casein, gelatin, polysaccharides (e.g., powdered starch, gum arabic, cellulose derivatives, alginic acid), lignin derivatives, bentonite, and synthetic water-soluble polymers (e.g., polyvinyl alcohol, polyvinyl pyrrolidone, polyacrylic acid); and stabilizers such as PAP (isopropyl acid phosphate), BHT (2,6-di-tert-butyl-4-methylphenol), BHA (2-/3-tert-butyl-4-methoxyphenol), vegetable oils, mineral oils, fatty acids, and fatty acid esters.

The present composition can also be prepared by making each of the active ingredients into the respective formulations using the above formulation technique and then mixing these formulations.

The present composition thus formulated may be applied to soil or plants as such, or after diluted with water or other solvents. The present composition may also be used in admixture with other herbicides, in which case the herbicidal activity can be expected to be enhanced. The present composition can also be used together with insecticides, bactericides, fungicides, safeners, plant growth regulators, fertilizers, soil conditioners, or other agents.

The application amount of the present composition, although it may vary with the mixing ratio of flumioxazin to fluthiamide as the active ingredient compounds, weather conditions, formulation types, application timings, application methods, application places, weeds to be controlled, and crops to be protected, is usually in the range of 5 to 5000 g as the total amount of active ingredient compounds per hectare. In the case of emulsifiable concentrates, wettable powders, flowables, some kinds of granules or other similar formulations, they are usually applied after diluted in their prescribed amounts with water at a ratio of 100 to 1000 liters per hectare. Granules and the like can be applied as they are, without diluting.

The following will describe formulation examples, in which parts are by weight.

FORMULATION EXAMPLE 1

Five parts of flumioxazin, 40 parts of fluthiamide, 3 parts of calcium lignin sulfonate, 2 parts of sodium laurylsulfate, and 50 parts of synthetic hydrated silicon oxide are well pulverized and mixed to give a wettable powder.

FORMULATION EXAMPLE 2

Eight parts of flumioxazin, 64 parts of fluthiamide, 3 parts of calcium lignin sulfonate, 2 parts of sodium laurylsulfate, and 23 parts of synthetic hydrated silicon oxide are well pulverized and mixed to give a wettable powder.

FORMULATION EXAMPLE 3

Forty parts of flumioxazin, 40 parts of fluthiamide, 3 parts of calcium lignin sulfonate, 2 parts of sodium laurylsulfate, and 15 parts of synthetic hydrated silicon oxide are well pulverized and mixed to give a wettable powder.

FORMULATION EXAMPLE 4

Twenty-five parts of flumioxazin, 10 parts of fluthiamide, 3 parts of calcium lignin sulfonate, 2 parts of sodium laurylsulfate, and 60 parts of synthetic hydrated silicon oxide are well pulverized and mixed to give a wettable powder.

FORMULATION EXAMPLE 5

Three parts of flumioxazin, 24 parts of fluthiamide, 3 parts of polyoxyethylene sorbitan monooleate, 3 parts of CMC (carboxymethylcellulose), and 67 parts of water are mixed and wet pulverized until the particle size comes to 5 microns or smaller to give a flowable.

FORMULATION EXAMPLE 6

Five parts of flumioxazin, 40 parts of fluthiamide, 3 parts of polyoxyethylene sorbitan monooleate, 3 parts of CMC (carboxymethylcellulose), and 49 parts of water are mixed and wet pulverized until the particle size comes to 5 microns or smaller to give a flowable.

FORMULATION EXAMPLE 7

Twenty parts of flumioxazin, 20 parts of fluthiamide, 3 parts of polyoxyethylene sorbitan monooleate, 3 parts of CMC (carboxymethylcellulose), and 54 parts of water are mixed and wet pulverized until the particle size comes to 5 microns or smaller to give a flowable.

FORMULATION EXAMPLE 8

Thirty parts of flumioxazin, 10 parts of fluthiamide, 3 parts of polyoxyethylene sorbitan monooleate, 3 parts of CMC (carboxymethylcellulose), and 54 parts of water are mixed and wet pulverized until the particle size comes to 5 microns or smaller to give a flowable.

The following will describe test examples.

Evaluation Criteria

The herbicidal activity is evaluated at 11 levels with indices of 0 to 10, i.e., shown by numeral "0", "1", "2", "3", "4", "5", "6", "7", "8", "9", or "10", wherein "0" means that there was no or little difference in the degree of germination or growth between the treated plants and the untreated plants at the time of examination, and "10" means that the test plants died completely or their germination or growth was completely inhibited. The herbicidal activity is excellent when ranked at "7", "8", "9", or "10", but insufficient when ranked at "5" or lower. The phytotoxicity is shown by "no injury" when no significant phytotoxicity was observed; "low" when low phytotoxicity was observed; "moderate" when moderate phytotoxicity was observed; or "high" when high phytotoxicity was observed.

Test Example 1

An emulsifiable concentrate of flumioxazin was prepared by well mixing 2.5 parts of flumioxazin, 16.25 parts of TOXANON P8L (trademark of Sanyo Chemical Industries) and 81.25 parts of cyclohexanone, and an emulsifiable concentrate of fluthiamide was prepared by well mixing 2.5 parts of fluthiamide, 16.25 parts of TOXANON P8L (mentioned above) and 81.25 parts of cyclohexanone.

Plastic pots each having an area of 18×20 cm$^2$ and a depth of 7.5 cm were filled with upland soil, and then seeded with soybean, corn, velvetleaf, ivyleaf morningglory, prickly sida, common cocklebur, pale smartweed, jimsonweed, common purslane, southern crabgrass, giant foxtail, and barnyardgrass. The emulsifiable concentrate of flumioxazin, the emulsifiable concentrate of fluthiamide, and a mixture of the emulsifiable concentrate of flumioxazin and the emulsifiable concentrate of fluthiamide were independently diluted in their amounts as shown in Table below with water.

Each dilution was uniformly sprayed on soil surface with a small sprayer. After the application, the test plants were grown in the greenhouse for 11 days, and the safety to soybean and corn and the herbicidal activity to weeds were then examined. The results are shown in the following table.

| Compound | Dosage (g/ha) | Plant to be treated | | | | | | | | | | | |
|---|---|---|---|---|---|---|---|---|---|---|---|---|---|
| | | a | b | c | d | e | f | g | h | i | j | k | l |
| Fluthiamide | 2.5 | no injury | no injury | 0 | 0 | 0 | 0 | 0 | 0 | 0 | 1 | 1 | 0 |
| Fluthiamide | 10 | no injury | no injury | 0 | 0 | 0 | 0 | 0 | 0 | 0 | 2 | 2 | 0 |
| Flumioxazin | 20 | no injury | no injury | 7 | 2 | 3 | 2 | 7 | 7 | 7 | 5 | 5 | 2 |
| Fluthiamide + Flumioxazin | 2.5 + 20 | no injury | no injury | 9 | 7 | 9 | 7 | 10 | 9 | 9 | 10 | 9 | 6 |
| Fluthiamide + Flumioxazin | 10 + 20 | no injury | no injury | 10 | 8 | 9 | 8 | 10 | 9 | 10 | 10 | 10 | 7 |

Note: Plants to be treated are shown by the symbols as follows
a: soybean
b: corn
c: velvetleaf
d: ivyleaf morningglory
e: prickly sida
f: common cocklebur
g: pale smartweed
h: jimson weed
i: common purslane
j: southern crabgrass,
k: giant foxtail
l: barnyardgrass

Industrial Applicability

A wide variety of weeds in upland field, particularly in corn fields and in soybean fields, can be effectively controlled by the present composition.

I claim:

1. A herbicidal composition comprising as active ingredients, (a) N-(7-fluoro-3,4-dihydro-3-oxo-4-prop-2-ynyl-2H-1,4-benzoxazin-6-yl)cyclohex-1-ene-1,2-dicarboxamide and (b) 4'-fluoro-N-isopropyl-2-(5-trifluoromethyl-1,3,4-thiadiazol-2-yloxy)acetanilide.

2. The herbicidal composition according to claim 1, wherein the weight ratio of the component (a) to the component (b) is 1:0.1 to 1000.

3. The herbicidal composition according to claim 1, wherein the weight ratio of the component (a) to the component (b) is 1:0.1 to 50.

4. The herbicidal composition according to claim 1, 2 or 3, for control of weeds i n soybean fields.

5. The herbicidal composition according to claim 1, 2 or 3, for control of weeds in corn fields.

6. A weeding method comprising applying a herbicidally effective amount of an herbicidal composition comprising (a) N-(7-fluoro-3,4-dihydro-3-oxo-4-prop-2-ynyl-2H-1,4-benzoxazin-6-yl)cyclohex-1-ene-1,2-dicarboxamide and (b) 4'-fluoro-N-isopropyl-2-(5-trifluoromethyl-1,3,4-thiadiazol-2-yloxy)acetanilide to weeds or place in which weeds will grow.

7. The weeding method according to claim 6 in soybean field.

8. The weeding method according to claim 6 in corn field.

9. The weeding method according to claim 6, wherein the total amount of the component (a) and the component (b) is 5 to 5000 g/ha.

10. The weeding method according to claim 6, wherein the weight ratio of the component (a) to the component (b) is 1:0.1 to 1000.

11. The weeding method according to claim 6, wherein the weight ratio of the component (a) to the component (b) is 1:0.1 to 50.

* * * * *